United States Patent
Khan et al.

(10) Patent No.: US 9,688,628 B1
(45) Date of Patent: Jun. 27, 2017

(54) DRUG REPOSITIONING: UREASE INHIBITORY ACTIVITY OF (2S)-1-[(2S)-2-METHYL-3-SULFANYLPROPANOYL]PYRROLIDINE-2-CARBOXYLIC ACID (CAPTOPRIL)

(71) Applicants: Jalaluddin Azam Jalal Khan, Jeddah (SA); Muhammad Iqbal Choudhary, Karachi (PK); Maryam Abdu Abdullah Al-Ghamdi, Jeddah (SA); Etimad Huwait, Jeddah (SA); Atia-tul Wahab, Karachi (PK); Samrah Iqbal, Karachi (PK)

(72) Inventors: Jalaluddin Azam Jalal Khan, Jeddah (SA); Muhammad Iqbal Choudhary, Karachi (PK); Maryam Abdu Abdullah Al-Ghamdi, Jeddah (SA); Etimad Huwait, Jeddah (SA); Atia-tul Wahab, Karachi (PK); Samrah Iqbal, Karachi (PK)

( * ) Notice: Subject to any disclaimer, the term of this patent is extended or adjusted under 35 U.S.C. 154(b) by 0 days.

(21) Appl. No.: 15/051,077

(22) Filed: Feb. 23, 2016

(51) Int. Cl.
*C07D 207/16* (2006.01)

(52) U.S. Cl.
CPC .................. *C07D 207/16* (2013.01)

(58) Field of Classification Search
CPC .................................... C07D 207/16
See application file for complete search history.

(56) References Cited

PUBLICATIONS

"Form snake venom to ACE inhibitor-the discovery and rise of captopril"—by Jenny Bryan, The Pharmaceutical Journal, vol. 282, p. 455 (Apr. 17, 2009).*
Stomach cancer—Mayoclinic.com—2012.*
"Diseases" (available online on Aug. 17, 2016).*
Howard Ansel (Pharmaceutical Dosage Forms and Drug Delivery Systems, Fifth Edition, Lea & Febiger (1990); p. 92-182).*

\* cited by examiner

*Primary Examiner* — Valerie Rodriguez-Garcia
(74) *Attorney, Agent, or Firm* — Sarfaraz K. Niazi

(57) ABSTRACT

This invention provides that (2S)-1-[(2S)-2-methyl-3-sulfanylpropanoyl]pyrrolidine-2-carboxylic acid (captopril) possess potent in vitro urease inhibitory potential with 95.00% inhibition and $IC_{50}=16.6\pm1.52$ μM, when compared to the standard inhibitor i.e. acetohydroxamic acid ($IC_{50}=41.5\pm1.50$ μM).

2 Claims, 2 Drawing Sheets

(2*S*)-1-[(2*S*)-2-Methyl-3-sulfanylpropanoyl]pyrrolidine-2-carboxylic acid (Captopril)

$IC_{50} = 16.6 \pm 1.52$ μM
$Ki = 9.28 \pm 0.0004$ μM (2S)-1-[(2S)-2-Methyl-3-sulfanylpropanoyl]pyrrolidine-2-
carboxylic acid (Captopril)

$IC_{50} = 16.6 \pm 1.52$ μM
$Ki = 9.28 \pm 0.0004$ μM

DRUG REPOSITIONING: UREASE INHIBITORY ACTIVITY OF (2S)-1-[(2S)-2-METHYL-3-SULFANYLPROPANOYL]PYRROLIDINE-2-CARBOXYLIC ACID (CAPTOPRIL)

BACKGROUND OF THE INVENTION

Drug repositioning or repurposing has received major interest in the past years. This approach increasingly enables scientists to discover potential pharmacological targets and to identify "new targets" of known drugs. It is found to be an attractive approach for efficient drug discovery and development, taking advantage of already available preclinical and clinical knowledge, thus allowing for considerable shortcuts in many steps in the drug development process. One important example of drug repositioning is colesevelam, originally developed as an adjunct to reduce low-density lipoprotein cholesterol (LDL-C) but now it is approved as a hypoglycemic agent for type 2 diabetes mellitus. Therefore, keeping the importance of this approach, our drug screening project is aiming to identify new drugs for lead optimization for different ailments. In the present studies, urease inhibitory assay was employed to evaluate the activity of (2S)-1-[(2S)-2-methyl-3-sulfanyl-propanoyl]pyrrolidine-2-carboxylic acid.

(2S)-1-[(2S)-2-methyl-3-sulfanylpropanoyl]pyrrolidine-2-carboxylic acid is an angiotensin-converting enzyme (ACE) inhibitor, and approved as drug (Captopril) for the treatment of hypertension, and heart failure. Captopril was developed and marketed by US drug company, "Squibb and Sons Pharmaceuticals". Its discovery and development was based on concepts pioneered by Nobel Laureate Prof. John Vane.

Besides its blood pressure-lowering properties, (2S)-1-[(2S)-2-methyl-3-sulfanylpropanoyl]pyrrolidine-2-carboxylic acid has various biological activities, such as immunomodulatory, beneficial effects on rheumatoid arthritis, prevention of complications in insulin-dependent diabetes mellitus, and anti-inflammatory properties (in schistosomiasis). Additionally it is found to be effective in lupus diseases, and autoimmune encephalomyelitis (EAE). Captopril was found to be capable of suppressing the production of monocytes/macrophage-derived proinflammatory cytokines (e.g. tumour necrosis factor (TNF), IL-1, IL-6, and IL-12). These immunomodulatory actions of captopril were due to different mechanisms, such as anti-proliferation, anti-oxidant, inhibition of metalloproteases, and elevation of prostaglandin. It is reported that these properties are related to the presence of thiol groups in its structure. (2S)-1-[(2S)-2-methyl-3-sulfanylpropanoyl]pyrrolidine-2-carboxylic acid has recently been found to inhibit Fas-induced apoptosis in human activated T cells and lung epithelial cells. It is also known to be used for the treatment of cysteine stones. The drug has a cysteine binding thiol group, resulting in the formation of captopril-cysteine complex, which is about 200 times more soluble than cysteine. Dose of 70-100 mg per day effectively reduces the formation of cysteine stones. Therefore, it is considered as a drug of choice in cysteine stone patents with history of hypertension.

Urease (amido-hydrolase, EC 3.5.1.5) is a large multimeric, $Ni^+$ containing metallo-enzyme. Ureases of plant and fungal origins are homo-oligomeric proteins, while the ureases of bacterial are heteropolymeric proteins. Biologically, it catalyzes the hydrolysis of urea into ammonia and carbamate. At physiological pH, carbamate spontaneously hydrolyzes into carbonic acid and ammonia. It plays an important role in nitrogen cycle, as it supplies nitrogen for seed germination and for the growth of microorganisms by facilitating breakdown of urea into ammonia. Beside this physiological role, it also has a pathological role in a wide range of diseases, such as urolithiasis, hepatic encephalopathy, hepatic coma, pyelonephritis, urinary catheter encrustation, gastritis, peptic, duodenal ulcers, and gastric cancers. Ammonia (released by the hydrolysis of urea) is one of the well-known causes of hepatic encephalopathy. Apart from causing diseases to human, it also causes several environmental and economic hazards in agriculture. Urease positive soil bacteria release ammonia in high quantity which not only deplete the urea, but also cause toxicity to plants. This scenario therefore demands discovery of effective inhibitors of urease enzyme.

Urease inhibitors are also required as drugs for the eradication of *Helicobacter pylori*, for the treatment of peptic ulcers, and other diseases, caused by ureolytic bacteria. Clinically used inhibitors against this enzyme include hydroxamic acid, bismuth complexes, and imidazole classes. However, these medicines have proved to be largely ineffective, and only a few have been approved for the use at clinical level. Search for new and effective inhibitors of urease is thus vigorously pursued in pharmaceutical research.

During the current study, Jack bean (*Canavalia ensiformis*) urease was used for in vitro biochemical evaluation, whose active site resembles to that of bacterial ureases with a bi-nickel nuclear center. The metallo-center comprises of two $Ni^{+2}$ ions, bridged by a carbamylated lysine residue and water molecule. One Ni ion is linked with two histidine residues and a terminal water molecule, while the second Ni ion is linked with the histidine residues, one aspartic acid residue, and water molecules. The mechanistic studies were carried out to determine the binding mechanism of (captopril) to urease.

BRIEF SUMMARY OF THE INVENTION

In continuation of our efforts very of new, effective, and safe urease inhibitors, in the present investigation, we evaluated the urease inhibitory potential of captopril ((2S)-1-[(2S)-2-methyl-3-sulfanylpropanoyl]pyrrolidine-2-carboxylic acid; Capoten), which is reported in the literature as angiotensin-converting enzyme (ACE) inhibitor.

Jack bean urease was used for the in vitro biochemical evaluation of (2S)-1-[(2S)-2-methyl-3-sulfanylpropanoyl] pyrrolidine-2-carboxylic acid (Captopril) as urease inhibitor. Mechanistic studies were carried out to determine the binding mechanism of the drug to urease. This is the first report describing the urease inhibitory activity of (2S)-1-[(2S)-2-methyl-3-sulfanylpropanoyl]pyrrolidine-2-carboxylic acid (Captopril).

DETAILED DESCRIPTION OF THE INVENTION

Figure 1:
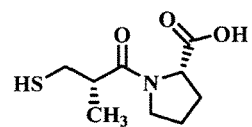
FIG. 1 depicts the structures of (2S)-1-[(2S)-2-methyl-3-sulfanylpropanoyl]pyrrolidine-2-carboxylic acid (captopril), and its the urease inhibitory potential.

Captopril was obtained from Glaxosmithklin (Pvt.) Ltd., Pakistan. Type IX Jack bean urease (EC 3.5.1.5), urea, and phenol were obtained from Sigma-Aldrich (USA). Sodium nitroprusside was purchased from Merck (Germany). Sodium hydroxide was purchased from Unichem (India). Sodium hypochlorite and HPLC grade methanol were purchased from BDH Lab. Supplies (UAE). Acetohydroxamic acid was obtained from MP Biomedicals (France).

The urease inhibition assay was performed spectrophotometrically in 96-well plate according to the method of Weatherburn at al., with slight modifications [20]. The solution of urease enzyme (1 U/well) was prepared in phosphate buffer (pH 6.8; 4 mM). As definition, one unit of urease enzyme liberates 1.0 μmol of $NH_3$ from urea per minute at pH 7.0 at 25° C. The total reaction volume was 200 μL per well. Reaction was performed in such a way that in each well 25 μL of urease enzyme was incubated with 5 μL of test compounds (250 μM for screening purpose and 250-31.25 μM for $IC_{50}$ determination) for 15 minutes, at 30° C. After 15 minutes, 55 μL of urea (100 mM) was added and 96-well plate was again incubated for 10 minutes at 30° C. After completion of 10 minutes, 45 μL of phenol (1% w/v phenol and 0.005% w/v sodium nitroprusside), and 70 μL of alkali reagents (0.5% w/v sodium hydroxide and 0.1% sodium hypochlorite) were added to each well. The plate was then again incubated for 50 minutes at 30° C. Urease activity was measured with the rate of production of ammonia, and change in optical density was monitored for 50 minutes (at 630 nm) on microtiter plate reader (Spectra Max M5, Molecular Devices, CA, USA). Acetohydroxamic acid (Lithostat i.e. drug used for the treatment of urolithiasis) was used as the standard compound (clinical drug).

The percentage of inhibition of each compound was calculated by using the following formula:

$$\%In\exists inbition = 100 - \left(\frac{\text{Absorbance of test compound}}{\text{Absorbance of control}}\right) \times 100 \quad [1]$$

Mechanistic Studies

For mechanistic studies, urease enzyme solution (1 U/200 μL) was incubated with different concentrations of inhibitors for 15 min at 30° C. The reaction was initiated by adding different concentrations of substrate (0.5-4.0 mM), then phenol and alkali reagent were added and change in absorbance was measured for 50 minutes at 630 nm on microtitre plate reader (Spectra Max M5, Molecular Devices, CA, USA).

Statistical Analysis

The results were analyzed by using SoftMax Pro Software (Molecular Devices, CA, USA). The percentage inhibition was calculated from the following formula:

% Inhibition=100−(OD of Test Compound/OD of Control)×100

The $IC_{50}$ values were calculated by the EZ-Fit enzyme kinetics program (Perellela Scientific, Inc., Amherst, USA). Lineweaver-Burk plot, secondary plot, and Dixon plot were plotted by using Grafit 7 (Erithacus Software Limited, UK). Grafit 7 program was used to evaluate the correlation coefficients, slopes, and intercepts by linear regression analysis.

Figure 2A:
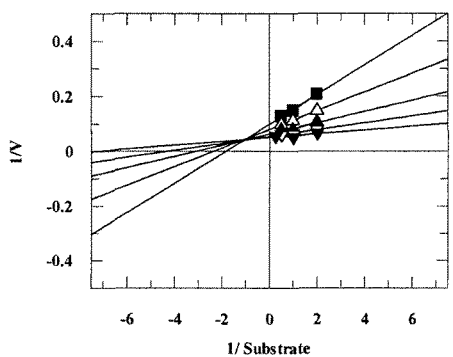
FIG. 2A depicts the lineweaver-Burk plot of (2S)-1-[(2S)-2-methyl-3-sulfanylpropanoyl]pyrrolidine-2-carboxylic acid, in which 1/s (inverse of substrate concentrations) is plotted on x-axis, while 1/v (inverse of Vmax values) is plotted on y-axis. Figure shows that apparent Km and Vmax have been change i.e. it is a mixed-type inhibitor.
Figure 2B:
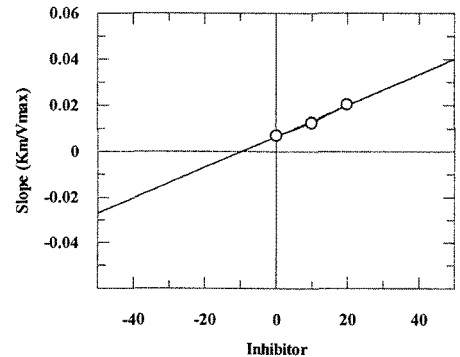
FIG. 2B depicts the double reciprocal plot for Ki determination which is between slope versus inhibitor concentrations.
Figure 2C:
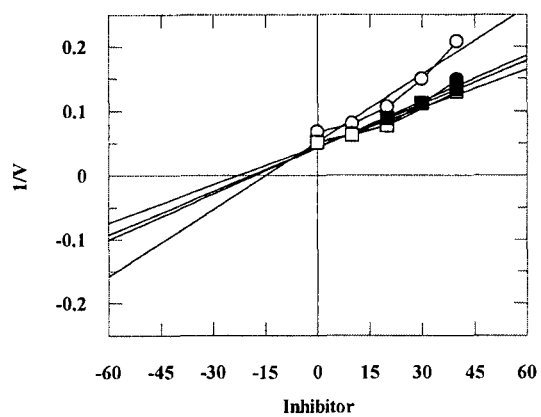
FIG. 2C depicts the Dixon plot there which plotted between 1/Vmax and [I], which indicate type of inhibition as a non-competitive against urease.

(2S)-1-[(2S)-2-methyl-3-sulfanylpropanoyl]pyrrolidine-2-carboxylic acid (Captopril) was found to be potent inhibitor of urease enzyme with $IC_{50}$=27±1.973 μM (FIG. 2), when compared to standard inhibitor i.e. acetohydroxamic acid ($IC_{50}$=41.5±1.50 μM). As per literature survay, this is the first report describing the urease inhibitory activity of this drug. It apparently seems that (2S)-1-[(2S)-2-methyl-3-sulfanylpropanoyl]pyrrolidine-2-carboxylic acid (Captopril) have possible sites for chelation with the Ni atom in the active site of the enzyme.

What is claimed is:

1. A method of treating urinary catheter encrustation comprising administering compound (2S)-1-[(2S)-2-methyl-3-sulfanylpropanoyl]pyrrolidine-2-carboxylic acid to a human or animal in need thereof.

2. A method of treating urinary catheter encrustation comprising administering a composition comprising compound (2S)-1-[(2S)-2-methyl-3-sulfanylpropanoyl]pyrrolidine-2-carboxylic acid combined with inert pharmaceutical ingredient(s) to a human or animal in need thereof.

\* \* \* \* \*